United States Patent [19]

Zai

[11] Patent Number: 4,583,260
[45] Date of Patent: Apr. 22, 1986

[54] COMBINED VACUUM CLEANER AND STEAM IRON

[76] Inventor: Re Chin Zai, No. 8, Ho-Chiang Street, San-Ming District, Kaohsiung, Taiwan

[21] Appl. No.: 733,540

[22] Filed: May 13, 1985

Related U.S. Application Data

[63] Continuation-in-part of Ser. No. 620,514, Jun. 14, 1984, abandoned.

[51] Int. Cl.⁴ .............................................. A47L 7/00
[52] U.S. Cl. ...................................... 15/328; 15/331; 15/320; 219/245; 38/75; 68/222
[58] Field of Search ............... 219/245, 271, 272, 275, 219/276, 284, 285, 286, 288, 289, 293, 295, 362, 373; 38/75, 88; 15/328, 330, 331, 320, 340; 34/90; 68/222

[56] References Cited

U.S. PATENT DOCUMENTS

| | | | |
|---|---|---|---|
| 1,868,170 | 7/1932 | Jasgur | 38/75 |
| 1,892,792 | 1/1933 | Thompson | 38/75 UX |
| 2,974,346 | 3/1961 | Hahn | 15/344 |
| 3,721,026 | 3/1973 | McCallum | 38/75 |
| 3,811,208 | 5/1974 | Vieceli et al. | 219/275 |
| 4,206,340 | 6/1980 | Osrow et al. | 219/295 |

FOREIGN PATENT DOCUMENTS

| | | | |
|---|---|---|---|
| 2396526 | 3/1979 | France | 219/373 |
| 8203643 | 10/1982 | PCT Int'l Appl. | 219/245 |

*Primary Examiner*—Philip R. Coe
*Assistant Examiner*—Frankie L. Stinson
*Attorney, Agent, or Firm*—Harding, Earley, Follmer & Frailey

[57] ABSTRACT

A combined vacuum cleaner and steam iron comprising a housing having a substantially flat bottom, which housing being provided with a chamber for containing water and another chamber for collecting dust, a heating device mounted in the water chamber by which steam is generated and thus discharged through a passage out of the water chamber, means for connecting various suction tubes, which means being formed integrally with the housing, a casing connected with the housing, in which casing a motor and a fan are provided for generating a suction force which is operable to introduce the dust through the suction tube into the dust chamber.

6 Claims, 8 Drawing Figures

COMBINED VACUUM CLEANER AND STEAM IRON

CROSS-REFERENCE

This is a continuation-in-part of the application Ser. No. 620,514 filed June 14, 1984, now abandoned.

BACKGROUND OF THE INVENTION

Generally, a conventional iron for pressing clothes is always so constructed that it can only be used for smoothing clothes. Similarly, the conventional vacuum cleaner also can only be used for cleaning floors, carpets or the like by drawing in air and dust together. However, it has been known that up to now there has no an apparatus able to function as a vacuum cleaner and a steam iron by means of a combination thereof.

SUMMARY OF THE INVENTION

The first object of the present invention is to provide a combination of steam iron and vacuum cleaner which is inexpensive in production and simple in construction.

The second object of the present invention is to provide a combination of steam iron and vacuum cleaner which is easily operated.

The third object of the present invention is to provide a combination of steam iron and vacuum cleaner comprising a housing having a substantially flat bottom, which housing being provided with a chamber for containing water and another chamber for collecting dust, a heating device mounted in the water chamber by which steam is generated and thus discharged from the bottom of the water chamber through a passage formed in the chamber, means for connecting various suction tubes, which means being formed integrally with the housing, a casing connected with the housing, in which casing a motor and a fan are provided for generating a suction force which is operable to draw dust through a suction tube into the dust chamber.

BRIEF DESCRIPTION OF THE DRAWINGS

One embodiment of the present invention will be described, by way of example, with reference to the accompanying drawings, in which.

DETAILED DESCRIPTION OF THE INVENTION

Figure 1:
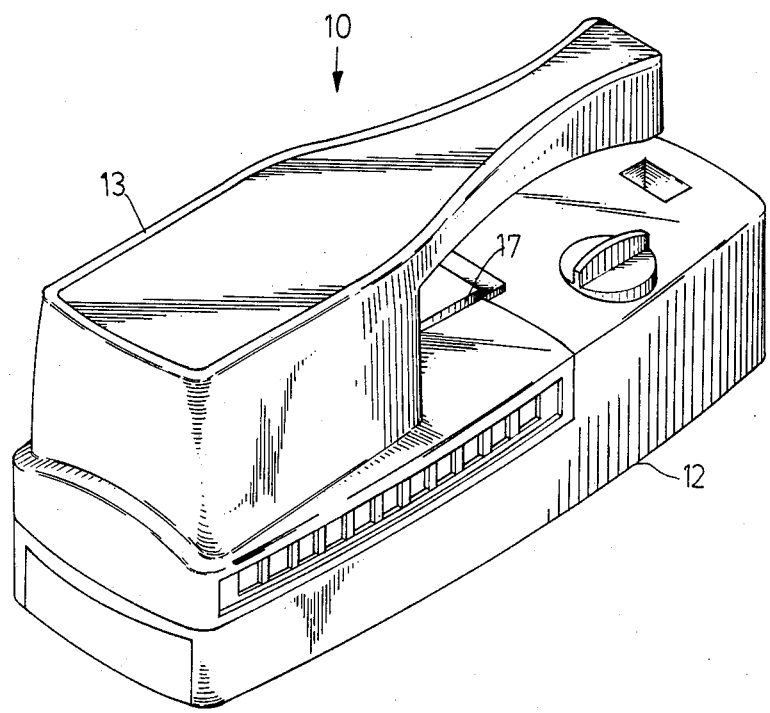
FIG. 1 is a perspective view of a combined vacuum cleaner and steam iron according to a preferred embodiment of the present invention.
Figure 5:
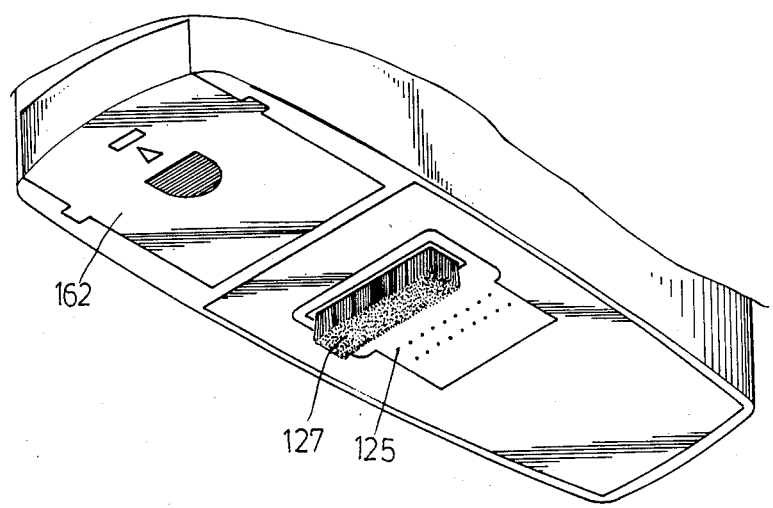
FIG. 5 is a perspective view analogous with FIG. 2, showing that a brush is received and held in a recess formed on the bottom of the housing.
Figure 6:
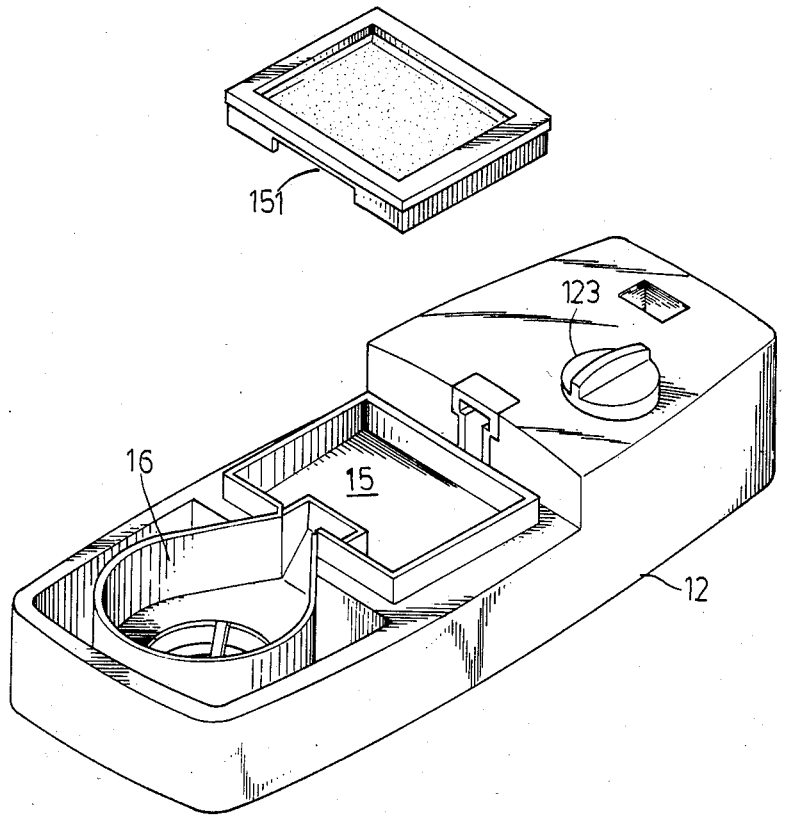
FIG. 6 is a perspective view of the housing according to the present invention.
Figure 8:
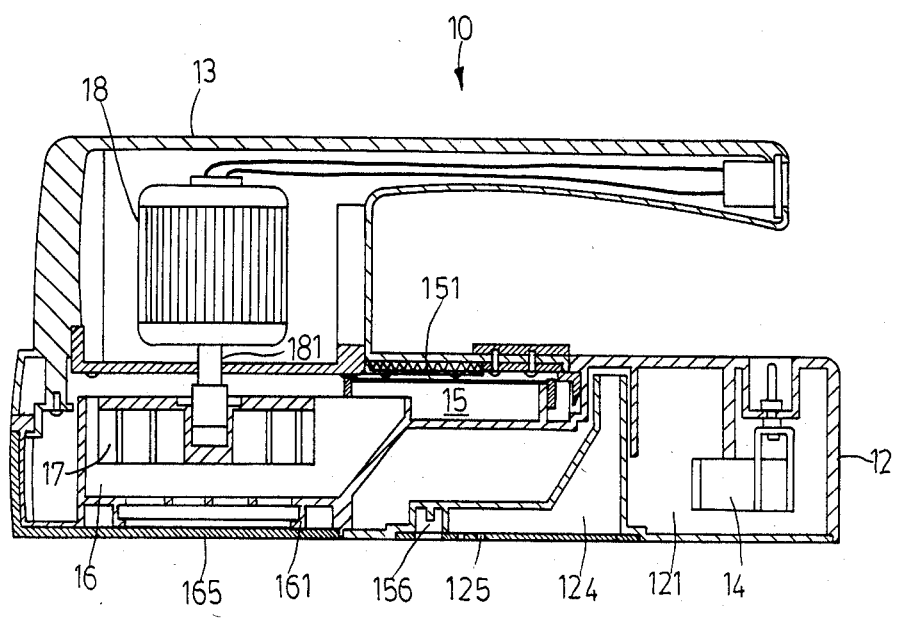
FIG. 8 is a vertically sectional view of the apparatus according to the present invention.

Referring now to the accompanying drawings, and initially to FIGS. 1 and 8, a combined vacuum cleaner and steam iron according to the preferred embodiment of the present invention is schematically illustrated and indicated generally at 10. The combined vacuum cleaner and steam iron 10 basically includes a housing 12 having a substantially flat bottom, and a casing 13 connected with the housing 12 by means of a snap means 17. With reference to FIGS. 6 and 8, the housing 12 is provided with a chamber 121 for containing water, in which chamber an electrical heating device 14 is mounted for heating the water contained in the water chamber 121. The water chamber 121 is provided with a water inlet enclosed by a liquid-tight cover member 123, and a steam passage 124 communicated with a plurality of holes 125 formed on the bottom surface thereof. In this manner, as the apparatus 10 according to the present invention being functioned as a steam iron, steam generated by heating the water contained in the water chamber 121 can pass through the passage 124 and discharge from the holes 125. Besides, the housing 12 is further provided on the bottom with a recess 126 which can receive a brush 127, as shown in FIG. 5, for cleaning clothes during ironing.

Figure 7:
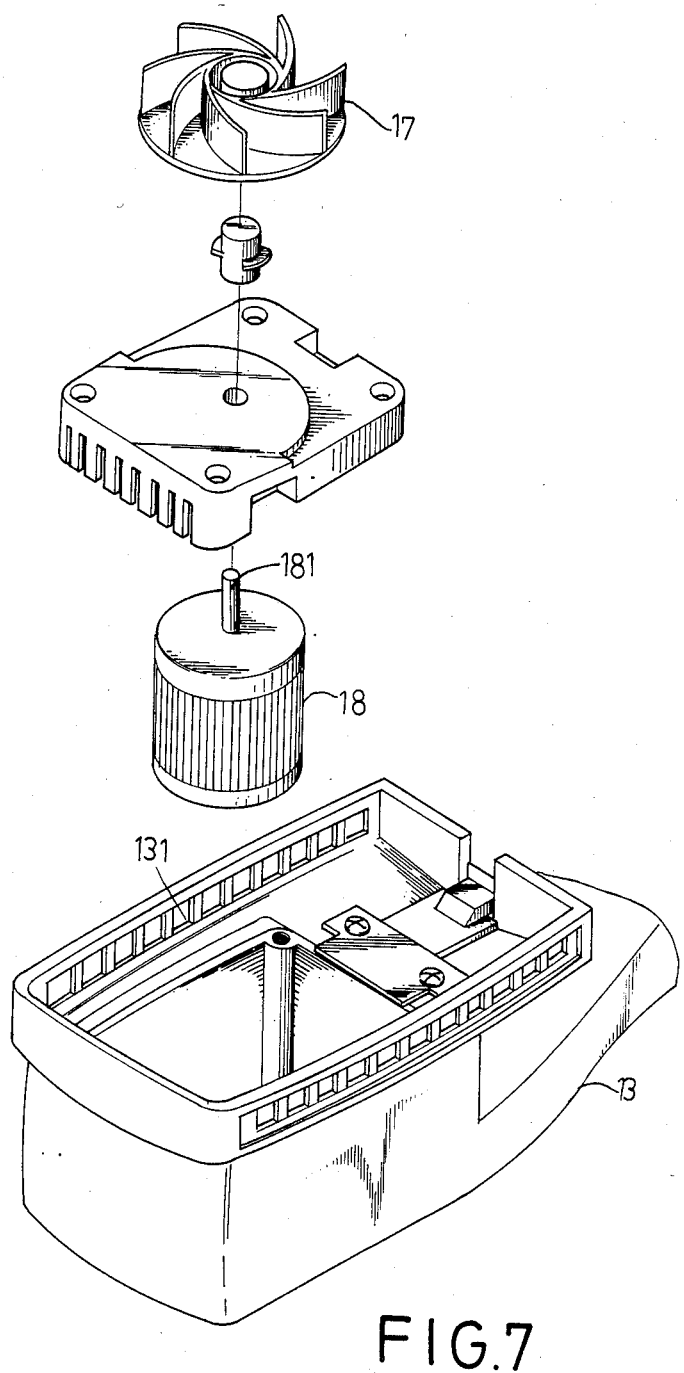
FIG. 7 is a segmantary view of the casing according to the present invention.

Referring now to FIGS. 6 to 8, a chamber 15 for collecting dust and a cylindrical recess 16 for receiving a fan 17 are formed on the housing 12. As shown in these drawings, the dust-collecting chamber 15 communicates with the cylindrical recess 16 and is provided with a detachable cover member 151 which is substantially a fabric screen edged by a frame of rigid material such as plastics material. A motor 18 is mounted with the casing 13, a transmission shaft 181 of which motor 18 is connected with a fan 17 which is normally located within the cylindrical recess 16. The casing 13 is provided around the sides thereof with slots 131 for dissipating heat energy generated by the motor 18.

Figure 2:
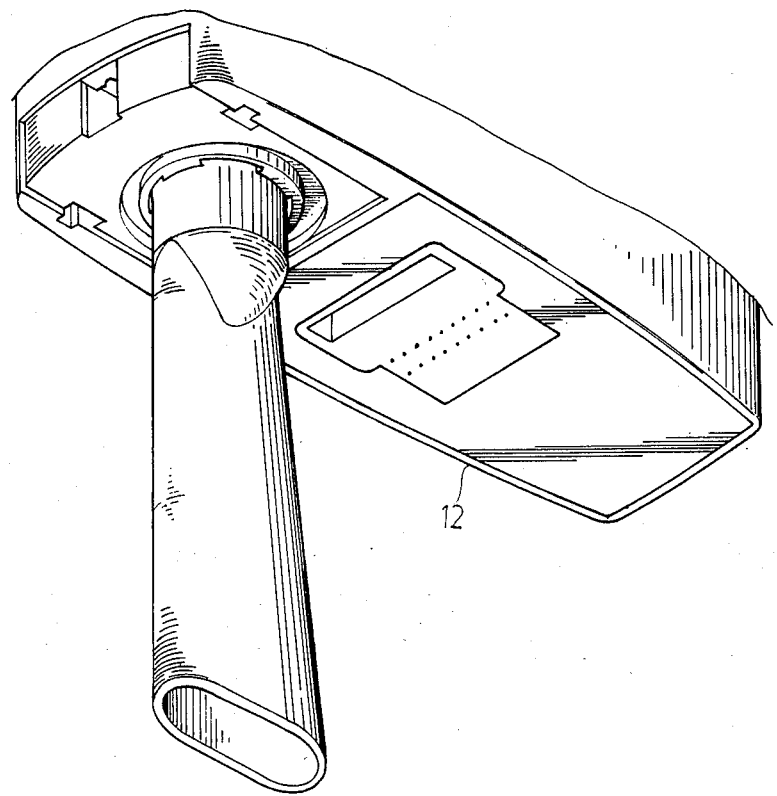
FIGS. 2 to 4 are fragmentary views showing that a suction tube is attached to a connecting means formed on the bottom of the housing.
Figure 3:
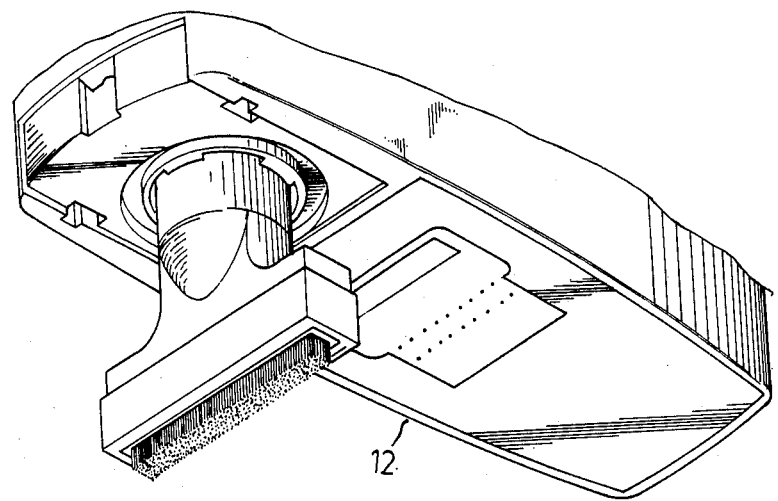
Figure 4:
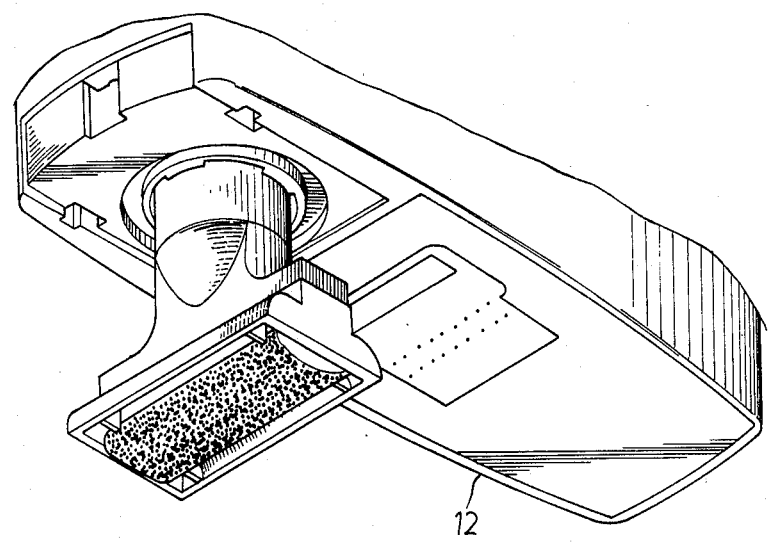

With reference to FIG. 8, the cylindrical recess 16 is open at the bottom end, around the open end of which recess 16 a connecting means 161 is formed integrally with the housing 12, which connecting means 161 can connect various suction tubes, as shown in FIGS. 2 to 4, when the apparatus 10 according to the present invention is intended to be functioned as a vacuum cleaner. Normally, the connecting means 161 and thus the open end of the cylindrical recess 16 is covered by a cover panel 162 when the apparatus 10 is functioned in a steam iron.

In operation, as shown in FIGS. 2 to 4 and 8, the rotation of fan 17 driven by the motor 18 causes air in the cylindrical recess 16 to be propelled into the dust-collecting chamber 15. Therefore, there is produced a suction force in the cylindrical recess 16 relative to the lower open end thereof and thus such suction force can be induced about the opening of the suction tube connected to the open end of the cylindrical recess 16. When air together with dust is sucked into the dust-collecting chamber 15 through the suction tube and the cylindrical recess 16, air will pass through the screen of the cover member 151 and dust will be gathered in the dust-collecting chamber 15. In the this manner, as shown in FIGS. 2 to 4, to adapt various cleaning works, a variety of suction tubes such as a tube having or not having a brush can be selectively applied to the connecting means 161 of the housing 12.

The present invention has been described in details above for purposes of illustration only and is not intended to be limited by this description or otherwise to exclude any variation or equivalent arrangement that would be apparent from, or reasonably suggested by the foregoing disclosure to the skill of the art.

I claim:

1. A combined vacuum cleaner and steam iron comprising a housing having a substantially flat bottom, said housing being provided with a chamber for containing water and another chamber for collecting dust, an electrical heating device mounted within said water chamber for heating the water contained in said water chamber, a casing connecting with said housing, a motor mounted within said casing, and a fan connected to a transmission shaft of said motor, said water chamber is provided with a passage which is communicated with a plurality of holes formed on the bottom of said housing whereby steam generated by heating the water contained in said water chamber can pass through said passage and discharge from said holes, said housing is further provided with a recess communicated with said dust-collecting chamber, which recess being provided for receiving said fan and being open at the lower end thereof, said fan is rotated by said motor and the rotation of said fan generates a suction force operable to draw air and dust through said lower open end of said recess into said dust-collecting chamber.

2. A combined vacuum cleaner and steam iron according to claim 1 wherein the bottom of said housing is further provided with a recess which may receive and hold a brush for cleaning clothes during ironing.

3. A combined vacuum cleaner and steam iron according to claim 1 wherein said casing is further provided around the sides thereof with slots for dissipating heat energy generated by said motor.

4. A combined vacuum cleaner and steam iron according to claim 1 wherein said water chamber is further provided with a water inlet and a liquid-tight cover member enclosing said water inlet.

5. A combined vacuum cleaner and steam iron according to claim 1 wherein said casing is connected with said housing by means of a snap means.

6. A combined vacuum cleaner and steam iron according to claim 1 wherein a connecting means is formed around the lower end of said recess receiving said fan, and wherein a suction tube can be attached to said connecting means.

* * * * *